United States Patent [19]
Abercrombie et al.

[11] Patent Number: 5,931,168
[45] Date of Patent: *Aug. 3, 1999

[54] APPLICATOR FOR COLORING HAIR OR FIBERS AND METHODS FOR MAKING AND USING SAME

[76] Inventors: Tracy Hill Abercrombie, 1229 ½ Smithwood Dr., Los Angeles, Calif. 90035; Douglas M. Whitaker, 8000 Turtle La., Ooltewah, Tenn. 37363

[*] Notice: This patent is subject to a terminal disclaimer.

[21] Appl. No.: 09/060,269

[22] Filed: Apr. 14, 1998

Related U.S. Application Data

[63] Continuation-in-part of application No. 08/839,678, Apr. 15, 1997.

[51] Int. Cl.$^6$ .............................. A45D 24/00; A61K 7/13
[52] U.S. Cl. .......................................... 132/208; 132/221
[58] Field of Search ..................................... 132/200, 208, 132/221, 222, 108, 109, 110; 401/54; 424/62, 70.6

[56] References Cited

U.S. PATENT DOCUMENTS

| | | | |
|---|---|---|---|
| 2,299,985 | 10/1942 | Hudson | 132/221 |
| 3,910,290 | 10/1975 | Litman | 132/321 |
| 4,206,195 | 6/1980 | Bolich, Jr. et al. | 132/202 |
| 4,344,930 | 8/1982 | MacRae et al. | 424/401 |
| 4,594,362 | 6/1986 | Snith et al. | 510/281 |
| 4,658,839 | 4/1987 | Dallal et al. | 132/221 |
| 5,002,075 | 3/1991 | Kellett et al. | 132/108 |
| 5,121,762 | 6/1992 | DiPinto et al. | 132/221 |

*Primary Examiner*—Todd E. Manahan
*Assistant Examiner*—Eduardo C. Robert
*Attorney, Agent, or Firm*—Albert O. Cota

[57] ABSTRACT

An applicator (100) for transferring color-altering material from a substrate to hair or fibers, and methods for making and using the same. The applicator (100) includes a first portion (102) and a contiguous second portion (106). A color-altering dye material (104), which is soluble in water and water-activated, is adhered to one or both portions (102,106) of the applicator (100). The applicator (100) is flexible, thin, and is made of a material such as a foil, a paper composition or a synthetic polymer which is conformable to the shape of the human hand. The color of the dye can be the same, different, or a combination thereof. Use of the applicator (100) requires wetting the hairs or fibers, and then applying the substrate to the hairs or fibers. Next, the user wraps the substrate about the bundle of hair or fibers, and firmly squeezes and/or wipes the encircling substrate against the bundle.

16 Claims, 3 Drawing Sheets

APPLICATOR FOR COLORING HAIR OR FIBERS AND METHODS FOR MAKING AND USING SAME

CROSS REFERENCE TO RELATED APPLICATION

This application is a continuation-in-part of application Ser. No. 08/839,678 filed Apr. 15, 1997.

TECHNICAL FIELD

The present invention relates to processes and devices for coloring hair or fibers, and more particularly to apparatus for applying coloring material to hairs on the body or fibers in textile materials, including methods for making and using the apparatus.

BACKGROUND ART

Apparatuses and processes for applying color-altering materials, such as dyes, to hair or fibers for the purpose of temporarily or permanently dyeing is well-known in the prior art. In the case of hair, such as human hair, the purpose typically is to cover unsightly or undesired indicators of aging. In the case of fibers, such as textile fibers, the purpose might be to cover stains or to resurrect old and faded products.

Typically, the color of hair or fibers can be altered through the use of rinses, sprays, lotions or creams. When darkening the hair, the coloring material usually takes the form of a dye; when lightening hair, a bleach and activator combination, along with a toner is utilized. Regardless of the coloring material that is used, they are applied in a step-by-step manner, often requiring a waiting period to allow the chemicals in the coloring material to react and for the materials to bond with the hair.

Against this background of known technology, the applicants have developed a new, more efficient, speedier, and cost-effective technique for applying coloring material to hair or fibers which can be performed outside the confines of a salon (hair) or factory (textiles), and by persons of little or no training.

More particularly, the applicants have invented a dye-bearing substrate and a method of making and using such. The substrate is constructed in such a manner as to enable the transfer of dye material to the hair or fibers without requiring the user to mix or touch the dye or other chemicals carried by the substrate.

A search of the prior art did not disclose any patents that read directly on the claims of the instant invention, however the following U.S. patents are considered related:

| U.S. Pat. No. | INVENTOR | ISSUED |
| --- | --- | --- |
| 5,146,937 | Lefebvre | September 15 1992 |
| 5,121,762 | DiPinto et al | June 16 1992 |
| 5,002,075 | Kellett et al | March 26 1991 |
| 2,140,682A (U.K.) | Sanders | December 5 1984 |
| 4,206,195 | Bolich, Jr. et al | June 3 1980 |

The U.S. Pat. No. 5,146,937 Lefebvre patent discloses the use of a sheet made of a polymer material having semi-flexible, thermally-insulating, hair-clinging, non porous, non slipping properties, as a dye-applying pad for hair highlighting. The polystyrene sheet defines one and another opposite flat portions merging about a fold line. A lock of hair is laid over one flat half portion of the sheet, and a fluid dye solution is applied to the lock of hair. The other flat half portion of the sheet is then folded over and flatly compressed against the first portion of sheet to take the locks in sandwich for a sufficient development time to enable permanent hair coloring.

The U.S. Pat. No. 5,121,762 DiPinto, et al patent discloses an end wrap comprising a substrate containing hair-waving chemicals. Also disclosed is a method for waving hair comprising applying end wraps having hair-waving chemicals to hair sections, activating the end wraps and dissolving the end wraps. A kit for use in the method is included.

The U.S. Pat. No. 5,002,075 Kellett, et al patent discloses a hair conditioning and styling pad which comprises a shaped body of a resilient, open-celled, hydrophilic polyurethane foam matrix integrally incorporating an aqueous phase incorporating about 70–90% water, about 5–25% of a hair conditioning agent, and a nonionic surfactant. The pad is preferably affixed to the tines of a styling brush or comb to yield a composite brush or comb which is effective to condition and style hair. In a further modification of the invention, color-modified aqueous phases further comprise about 5–25% of a temporary hair coloring agent, and the percentage of water in the color-modified aqueous phase will be about 60–80%.

The 2,140,682A Sanders (U.K.) patent discloses a hairdresser's masking sheet comprising a substrate of flexible material and securing means carried by the substrate. The sheet allows rapid and initial attachment to the strands of hair and effects rapid removal from the strands after treatment.

The U.S. Pat. No. 4,206,195 Bolich, Jr., et al patent discloses an article especially designed for conditioning hair. The article is comprised of a flexible substrate releasably carrying a hair conditioning agent and a water soluble salt. The article when rubbed onto hair provides combing, detangling, static fly-away and softness benefits. Additionally, the manageability of the hair is improved.

For background purposes and as indicative of the art to which the invention is related reference may be made to the remaining cited patents.

| U.S. Pat. No. | INVENTOR | ISSUED |
| --- | --- | --- |
| 4,658,389 | Dallal, et al | April 21 1987 |
| 4,594,362 | Smith, et al | June 10 1986 |
| 4,344,930 | MacRae, et al | August 17 1982 |
| 4,271,272 | Strickman, et al | June 2 1981 |
| 2,299,985 | Hudson | October 27 1942 |

DISCLOSURE OF THE INVENTION

An object of the present invention is to provide hair or fiber color applicators to which are affixed coloring dye, and methods for making and using such applicators, while overcoming many drawbacks and disadvantages of other color applicators known in the art.

Another object of the invention is to provide novel methods for securing water-activated dye on a thin, flexible substrate, with the dye residing on the substrate in a predetermined pattern or configuration.

Still another object of the invention is to provide an applicator tool for transferring dye from one surface to another, where the one surface comprises a substrate to which the dye is affixed and the other surface comprises the exterior of fibers, such as human hair or textiles. The substrate preferably comprises a flexible material which is configured for comfortable support when held in the human hand. The substrate material can consist of a thin sheet of paper, plastic, fabric or metal, foil or a sponge, a cotton ball or a cosmetic puff. The dye or colorant is preferably affixed to only one side of the substrate so as to avoid transfer of the dye to the hand during application. In one embodiment, the substrate comprises at least a first and second side, wherein the second side is foldable over the first side, thereby protecting the hand from contact with the dye as the product is being applied.

Yet another object of the invention is to provide a plurality of applicator tools, each comprising a flexible substrate conformable to a human hand wherein on one or both portions of the substrate is secured a dye material. Two or more of the plurality of tools are preferably packaged together as a set or kit.

These and other objects of the present invention are achieved in accordance with the color applicator which includes a dye material adhered to one or two portions of a substrate. The dye material is preferably soluble in water and water-activated, and is carried by a portion of the substrate. Two processes for fabricating the applicators are disclosed.

Each applicator carries a dye material which has a specific color. The applicators are packaged singly, or they may be packaged together as a kit with the color of dye on the applicators being the same, different, or a combination thereof.

Use of an applicator involves either wetting a bundle of hairs or fibers to be colored, or wetting the substrate containing the dye, or wetting both hair/fiber and substrate, and contacting the dye-containing portion of the substrate with the surface to be colored, cradling the substrate in the hand so that the substrate can conform to the shape of the hand. In one embodiment, for example when touching up the rootline of the hair is desired, the dye-containing portion of the substrate is simply rubbed against the root area to be colored. In an alternate embodiment if it is desired to cover the entire surface of a hair or fiber bundle, the user wraps the substrate about the bundle of hair or fibers, and firmly squeezes and/or wipes the side of the encircling substrate containing the dye onto the bundle of fibers or hair.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
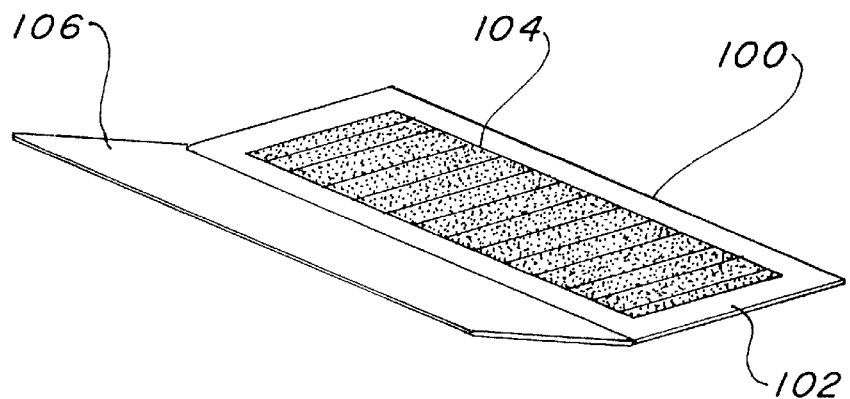
FIG. 1 shows a color applicator in accordance with the present invention.
Figure 7:
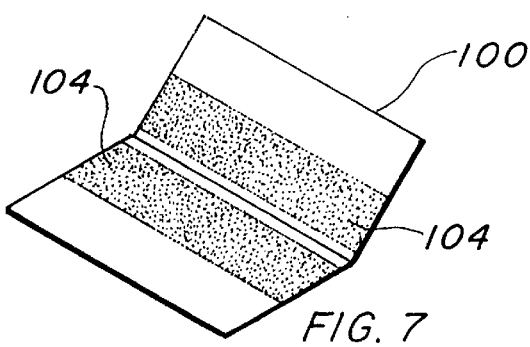
FIG. 7 illustrates a second embodiment with the layer of dye material deposited on the first and second side.
Figure 8:
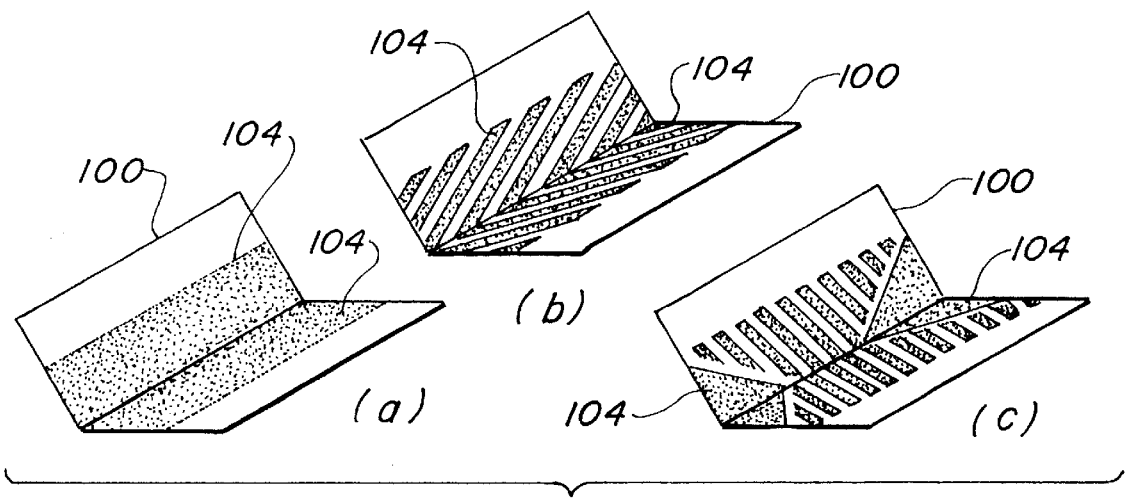
FIGS. 8a–8c show the second embodiment in a partial folded position with three exemplary patterns for the layer of dye material on both portions of the first side.

The best mode for carrying out the invention is presented in terms of a preferred embodiment that is disclosed in two designs. In both designs, an applicator 100 is used that comprises a substrate having a first portion 102 and a contiguous second portion 106 that folds over the first portion. In the first design, as shown in FIG. 1, a layer of dye material 104 is deposited only on the first portion 102 while in the second design, as shown in FIGS. 7 and 8, a layer of color-altering material is deposited on both the first portion 102 and the second portion 106.

The substrate is preferably a thin, flexible, conformable material, such as paper or paper composition, plastic or a foil which can include a metal or saran. The color-altering material is preferably a dry particulate or a powder, color-altering composition or compound that is water soluble and water-activated.

Figure 2:
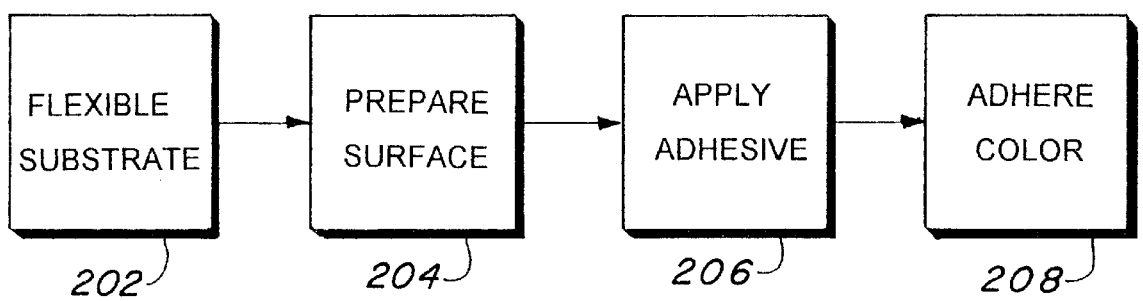
FIG. 2 is a flow chart showing a sequence of steps of a first process for making a color applicator in accordance with the teachings of the present invention.

Generally, the present invention contemplates fabrication of the applicator 100 by color-adhering material to the substrate using a binder material. FIG. 2 of the drawings is a flow chart depicting a sequence that is followed to carry out a process utilizing an applicator of the type shown in FIGS. 1 and 7.

The first block 202 of FIG. 2 depicts the substrate. The second block 204 represents the step of preparing one surface of the substrate for receipt of a first adhesive material. The preparation contemplated for this step involves smoothing and cleaning the surface.

The third block 206 represents the step of applying the adhesive material to the one surface of the substrate. This is accomplished by spraying or brushing the adhesive onto the one surface of the substrate. The adhesive material can include an adhesive composition, such as glue or other similar adherents. The purpose of the adhesive material is to provide a tacky coating on the one portion of the substrate.

The fourth block 208 represents the step of covering the adhesive coating with a powdered or particulate, water soluble and water-activated, color-altering material. This can be accomplished by dusting or otherwise depositing the color-altering material on the adhesive coating.

The color-altering material may be any water-activated colorant that is acceptable for use on hair. The colorant may be temporary, semi-permanent, demi-permanent, or permanent and may also be either natural or synthetic. Examples of synthetic colorants useful with the applicator of the invention include, but are not limited to: water-activated HC, D & C, or FD & C colors, nitro dyes such as, nitro derivatives of aminophenols and phenylenediamines; or para-dyes, such as p-phenylene diamine, p-toluenediamine, p-aminophenyldiamine, p-aminophenol and derivatives thereof. Also, indamines and indophenols, and acid and basic colors, such as acid blues, browns, reds, yellows or oranges, and basic blues, greens, yellows, reds, violets, and brown can be used. An exemplary list of cosmetically acceptable hair colorants can be found in the International Cosmetic Ingredient Handbook, Third Edition, Cosmetic Toiletry and Fragrance Association, Washington, D.C., 1995, the contents of which are incorporated herein by reference. Naturally occurring colorants (and their active components) which may be used include, but are not limited to: water activated annatto extracts, saffron (crocin), grape color or grape skin extract (malvidin, delphenidin or cyanidin derivatives), beet extract, (betacyanins or betaxanthins) or henna. Useful colorant components are commercially available, for example, from Jos. H. Lowenstein & Sons, Brooklyn, N.Y. In certain cases, particularly when a permanent, or lightening, effect is desired, an oxidizing agent, such as hydrogen peroxide or sodium perborate, may also be employed.

A specific example of components of useful powders (GO Powders, available from Jos. H Lowenstein & Sons) which may be adhered to the flexible substrate, for the production of colors ranging from blond to black, would be: sodium sulfate, sodium perborate, xanthan gum, sodium silicate, silica, sodium lauryl sulfate, and any one or all of the following colorants: 2-amino-6-chloro-4-nitrophenol, p-phenylenediamine sulfate, 4-amino-2-hydroxytoluene sulfate, 2-nitro-p-phenylenediamine sulfate, 2,6-diaminopyridine sulfate, m-aminophenol sulfate, 1,5-naphthalenediol, p-aminophenol sulfate, HC yellow No. 4, 2-chloro-p-phenylenediamine sulfate, 2,5-diaminotoluene sulfate, N,N-Bis(2-hydroxyethyl)-p-phenylenediamine sulfate.

An alternate powder composition is a "bright" powder, also available from Jos. H. Lowenstein & Sons, having the following composition: sodium sulfate, xanthan gum, silica, sodium lauryl sulfate and any one or all of the following colorants: HC yellow no. 4, FD & C blue no. 1, basic blue 9, 2-amino-6-chloro-4-nitrophenol, basic violet 14.

An additional component of the suspension to be applied to the substrate may be a hair conditioner. These materials are numerous and well known in the art, and include, for example, jojoba, cetrimonium chloride, quaternium and polyquaternium compounds, dimethicone copolyols, amodimethicone, and the like. An extensive, but not necessarily exhaustive, list of hair conditioners is found in the International Cosmetic Ingredient Handbook, supra, incorporated herein by reference.

The tacky adhesive coating, and hence the color-altering material, is preferably applied in a substantially geometrical pattern, such as a rectangle or square area. The coating may also be applied to a plurality of regions having shapes or configurations which are contiguous or spaced from one another with regularity or randomness. The coating configurations are designed to provide delivery or transference of the color-altering material to a bundle of hair or fibers in a maximized and in an efficient manner.

Figure 3:
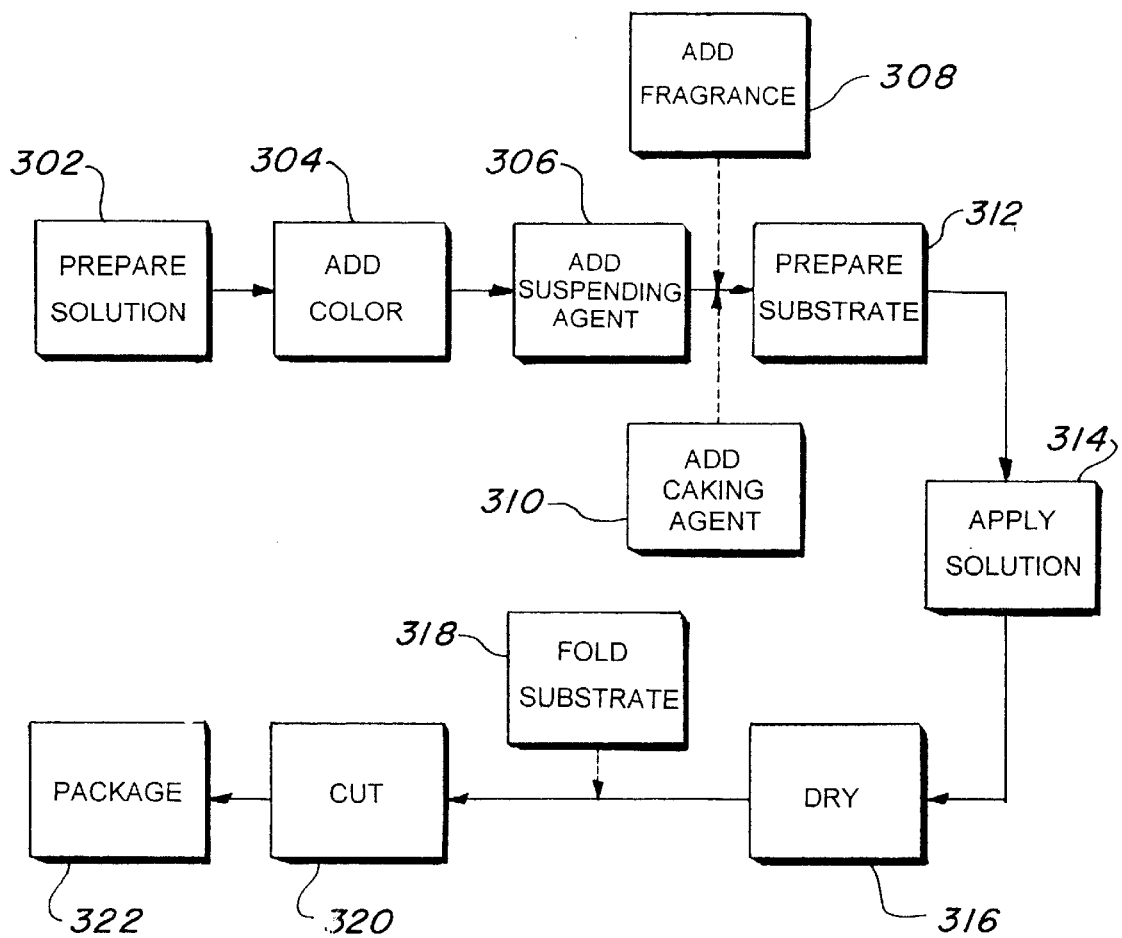
FIG. 3 is a flow chart showing a sequence of steps of a second process for making a color applicator in accordance with the teachings of the present invention.

FIG. 3 is a block diagram showing steps contemplated by a second process of the present invention. This process involves initially forming a dye-containing solution, and then applying the solution to a substrate.

The first block 302 represents a first step of preparing a solution of a film-forming polymer. The film-forming polymer must be soluble in water and alcohol and is chosen such that it possesses a mean molecular weight of between 10,000 and 700,000. Vinyl pyrrolidone polymers, vinyl pyrrolidone co-polymers or a combination thereof are preferred. Alcohols such as methanol, ethanol, 1-propanol, 2-propanol can be used alone or in combination with one another or in combination with a co-solvent. Co-solvents can be various esters, ethers or ketones. Methyl acetate, vinyl acetate, acetone, ethyl methyl ketone, dimethyl ether, isopropyl ether are examples of co-solvents. The polymer solution is preferably prepared as a 4–54 percent wt/wt solution in alcohol/co-solvent, with a 5–49 percent preferred.

Block 304 represents a second step of adding, under gentle agitation, a desired coloring compound to the polymer-ethanol solution at 11–54 percent of a known weight of the solution. This produces a suspension of coloring compound with a concentration of 10–49 percent.

Block 306 represents a third step of adding a suspending agent to the solution. Typical suspending agents comprise silicone, fumed silica, precipitated silica and the like. The suspending agent facilitates ease of handling during conventional printing processes when a coloring compound is deposited on a substrate. Preferably, the suspending agent is added at a rate of 0.6–5.0 wt/wt percent of the solution. The suspending agent maintains a homogeneous mixture of the solid coloring compound particles. The preferred concentration of suspending agent will depend on the type of printing process employed in depositing the solution on the substrate. For example, where the solution is to be deposited on a substrate using flexographic printing method, a 1.1–3.2 wt/wt percent of the color suspension is desirable.

Blocks 308 and 310 represent fourth and fifth steps of adding fragrances and a caking agent to the solution. The preferred caking agents comprise isopropyl myristate, silicone fluid, diethyl phthalate or petroleum distillates. These caking agents allow a greater deposition of color compound during the printing process. This might be necessary for compounds that produce lighter colors. Where the use of a caking is indicated, a 0.4–2.3 wt/wt percent of a water insoluble/alcohol soluble oil or oily compound is preferably added.

Block 312 depicts the step of preparing the substrate for receipt of the solution. Although shown in FIG. 3 as a step following preparation of the solution, it is clear that the step of preparing the substrate can be performed before the solution is made.

The substrate to which the solution is to be applied is preferably a thin flat sheet of a flexible material formed from paper, plastic, fabric or a metal foil. Also, the substrate can consist of a sponge, a cotton ball or a cosmetic puff. Preparation of the substrate includes one or more steps of smoothing, cleaning and drying the portion onto which the solution is to be applied. Further, the step of preparing the substrate can include the application of a moisture impermeable coating to the surface of the substrate on which the solution is to be applied such coatings include wax, saran, polyester, ultra violet cured coatings and latex coatings. These moisture impermeable coatings prevent the coloring compound from passing through the substrate and staining the user's hands or fingers. Latex based or latex impregnated paper stocks can be employed as well as commercial "wet strength" paper stocks.

Referring now to block 314 of FIG. 3, the process contemplates the further step of applying the solution to the substrate via conventional printing methods, such as flexographic printing, gravure, silkscreen, offset printing, web offset, etc. One method of application of the solution to the substrate is by the web offset process, which utilizes a flexographic apparatus. In this method, a continuous roll of a selected paper substrate is carried on a web press which includes an in-line finishing roll.

Printing can take place on both sides of the web. on a first side of the web, the coloring compound solution is deposited. On a second side of the web, the printing can take the form of text, such as instructions for use or disposal, and/or graphics, such as the manufacturer's logo or illustrations depicting use and handling. Either side may also be provided with a colored background. The color-altering solution is preferably printed on the first side of the substrate in the form of either a single strip or opposing strips covering an elongated portion of the substrate. Where the substrate is an elongated web that is to be folded in half lengthwise, less than 0.5 inch (1.27 cm) of the web width is printed with the coloring compound in one design and essentially the full width in the second design. The printed strip of coloring compound can be any size, but between 0.375 (0.953 cm) and 2 inches (5.08 cm) has been found preferable for economy and efficiency. Once the strip of coloring compound is applied, the substrate is immediately passed through a gas-fired forced-air print drier.

Figure 5:
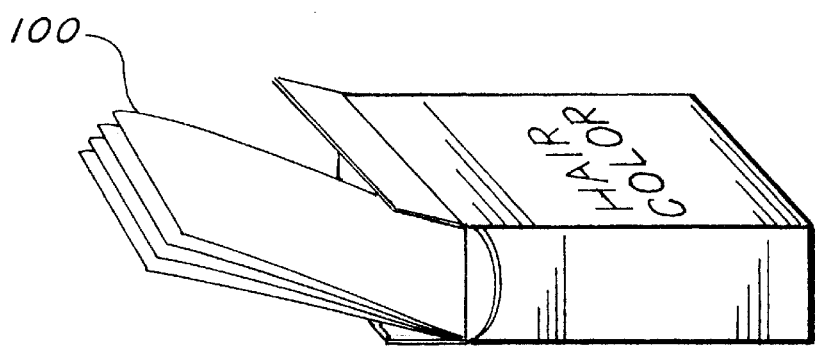
FIG. 5 shows plural applicators being inserted into a box for packaging as a kit.

When dried, the substrate may be folded, as shown in block 318, so that the hair color can be contained inside a folder. Whether or not folded, the web can then be cut, as shown in block 320, into individual pieces, and packaged, as shown in block 322, individually or with other pieces having the same or different colors as a kit as shown in FIG. 5.

Figure 6:
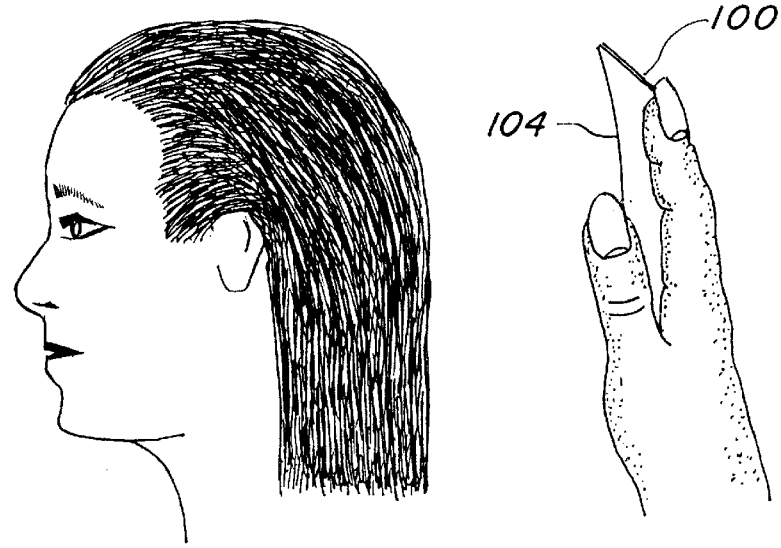
FIG. 6 shows an applicator in a user's hand while being used to color hair on another person's head.

Use of the applicator 100 preferably involves wetting the bundle of hair or fibers, which have been identified for coloring, and then interposing the substrate between the user's hand and the hair or fibers to be colored, cradling the substrate in the hand so that the substrate can conform to the shape of the user's hand as shown in FIG. 6. Next, the user either presses the substrate against the wet hair and contemporaneously moves the substrate relative to the hair or fibers with a wiping motion, or wraps the substrate about the hair or fibers while firmly squeezing the hair or fibers within the encircling substrate.

Use of the applicator 100 can also be achieved by first wetting the applicator itself, as for example with a mist of water or steam, and then pressing or squeezing it against hair or fibers. The initial dampening of the applicator, or the contact of a dry applicator with wet hair, will cause the water-activated dye particles to mix with the water, forming a dye-containing solution on the surface of the substrate, which is contacted with the hair or fibers.

The squeezing and/or wiping motion of the substrate relative to the hair or fibers enables the dye-containing coloring compound to be transferred to the hair or fibers.

Figure 4:
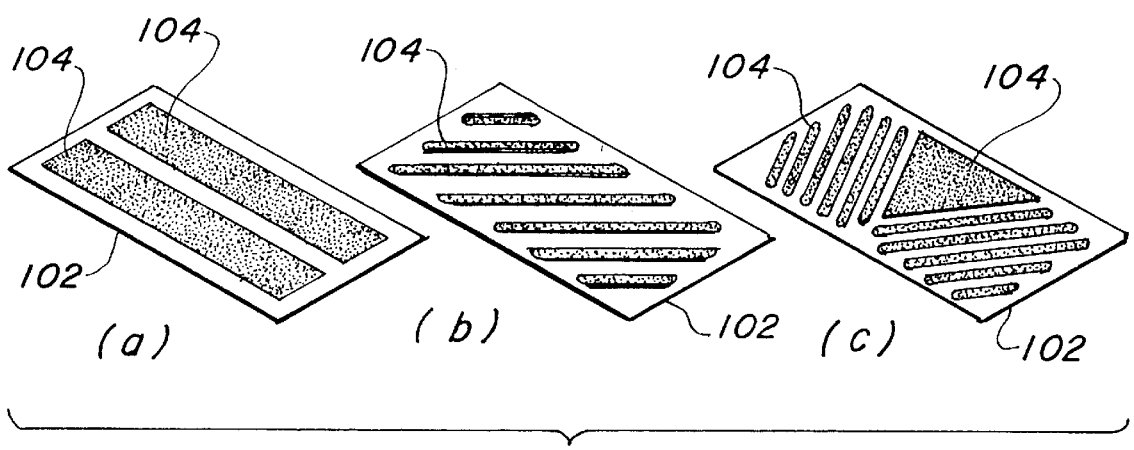
FIGS. 4a–4c show three exemplary patterns which have proven effective for coloring the bundle of hair or fibers.

The applicator and method for making such, as described above in connection with the present invention, involves the deposition of the color-altering compound solution on the substrate web in a variety of patterns and designs, by processes similar to those depicted in FIGS. 2 and 3. Three exemplary patterns are shown in FIGS. 4a–4c. In FIG. 4a spaced rectangles are shown, in 4b parallel lines are shown and, in 4c chevrons are shown. Further, FIGS. 8a, 8b and 8c illustrate the respective patterns that can be utilized. Other patterns and designs can include spaced and/or juxtaposed circles, grids, and dots. The coloring composition that can be used with the applicator of the present invention and in the methods for making the applicator can include temporary, semi-permanent, demi-permanent or permanent hair color compounds, bleaching compounds, or conditioning hair coloring compounds.

It will be noted that both designs of the preferred embodiment are basically the same and differ only in the addition of the layer of color-altering material 104 on portion 106 as both designs are eventually folded in half for application of the dye to the hair or fibers either by the user's hand or folded mechanically as shown in block 318 prior to packaging.

While the present invention has been described in conjunction with specific embodiments thereof, it is evident that many alternatives, modifications and variations will be apparent to those skilled in the art in light of the foregoing description. Accordingly, the present invention is intended to embrace all alternatives, modifications and variations which fall within the spirit and scope of the appended claims.

We claim:

1. A method of making an applicator for coloring hair or fibers, comprising the steps of:
   a) providing a flexible substrate having a first side and a second side,
   b) adhering water-activated color-altering material to said first side of said substrate, and
   c) folding said first side over said second side acting as a protective cover for a human hand.

2. The method as specified in claim 1 wherein said step of adhering color-altering material to said substrate first side comprises first applying a binder material to said first side.

3. The method as specified in claim 2 wherein said step of applying a binder material to said first side comprises spraying a tacky substance on said side.

4. The method as specified in claims 3 wherein said step of applying a binder material further comprises the steps of depositing said color-altering material atop said binder material and then drying said binder material.

5. The method as specified in claim 1 and including the further step, before adhering said color-altering material on said substrate, of preparing a solution of water-soluble film forming polymer in alcohol, where the polymer possesses a mean molecular weight of between 10,000 and 700,000.

6. The method as specified in claim 5 and further including the step of adding the color-altering material to said solutions.

7. The method as specified in claim 6 and further including the step of adding to said solution a suspending agent.

8. The method as specified in claim 7 wherein said suspending agent comprises silicone, fumed silica, or a precipitated silica.

9. The method as specified in claim 7 and further including the step of adding to said solution a fragrance.

10. The method as specified in claim 7 and further including the step of adding to said solution a caking agent.

11. The method as specified in claim 10 wherein said caking agent comprises isopropyl myristate, silicone fluid, diethyl phthalate or petroleum distillates.

12. An applicator for transferring color-altering material to strands of hair or fibers, comprising:
   a) a flexible substrate having a first side and a second side, wherein the second side is conformable to a human hand, and the first side of said substrate defines a first portion and a second portion with the first portion bearing said color-altering material and the second portion devoid of said material, and
   b) a water-activated color-altering material affixed to said first side of said substrate.

13. A method of making an applicator for coloring hair or fibers, comprising the steps of:
   a) providing a flexible substrate having a first side and a second side,
   b) adhering water-activated color-altering material to said first side of said substrate, wherein the step of adhering comprises printing said color-altering material on said first side, and,
   c) folding said first side over said second side acting as a protective cover for a human hand.

14. A method for coloring hair, comprising the steps of:
a) wetting either;
   (1) the hair to be colored;
   (2) a flexible substrate to which a water-soluble hair dye is affixed; or
   (3) both hair and substrate;
b) folding said substrate around the hair,
c) contacting the hair with a portion of the substrate to which the dye is affixed, and
d) maintaining contact between the substrate and the hair for a period of time sufficient to transfer the hair dye from said substrate to said hair.

15. The method as specified in claim 14 wherein said step of contacting said wet hair comprises moving the substrate relative to said hair so that said transfer of hair dye to said hair can be effected.

16. The method as specified in claim 15 wherein said substrate is a thin, flexible sheet that is conformable to a human hand, and said method further comprises the further steps of grasping a bundle of hair fibers so that said substrate encircles said bundle, and squeezing said bundle encircled by said substrate.

* * * * *